(12) United States Patent
Nagano et al.

(10) Patent No.: US 7,482,473 B2
(45) Date of Patent: Jan. 27, 2009

(54) COUMARIN DERIVATIVE

(75) Inventors: Tetsuo Nagano, Tokyo (JP); Yasuteru Urano, Kanagawa (JP); Takuji Shoda, Chiba (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 11/470,820

(22) Filed: Sep. 7, 2006

(65) Prior Publication Data
US 2007/0197778 A1 Aug. 23, 2007

(30) Foreign Application Priority Data
Feb. 6, 2006 (JP) ............................. 2006-027815

(51) Int. Cl.
*C07D 405/00* (2006.01)
(52) U.S. Cl. .................................. 548/525
(58) Field of Classification Search ........................ None
See application file for complete search history.

(56) References Cited
OTHER PUBLICATIONS

Brune et al., caplus an 1994:477054.*

* cited by examiner

*Primary Examiner*—Kamal A Saeed
*Assistant Examiner*—Sun Jae Y Loewe

(74) *Attorney, Agent, or Firm*—Greenblum & Bernstein, P.L.C.

(57) ABSTRACT

A compound represented by the following general formula (I) or a salt thereof [$R^1$ represents hydrogen atom, or a $C_{1-12}$ alkyl group; $R^2$ represents a $C_{1-12}$ alkyl group having one or more maleimide groups, an aryl group having two or more maleimide groups, a group represented by the formula (A): —$(CH_2)_n$—CO—N($R^{11}$)($R^{12}$) ($R^{11}$ and $R^{12}$ represent hydrogen atom, a $C_{1-12}$ alkyl group, a $C_{1-12}$ alkyl group having one or more maleimide groups, or an aryl group having one or more maleimide groups, and n represents an integer of 1 to 6), or a group represented by the formula (B): —$(CH_2)_m$—NH—CO—$R^{13}$ ($R^{13}$ represents a $C_{1-12}$ alkyl group having one or more maleimide groups, or an aryl group having one or more maleimide groups, and m represents an integer of 1 to 6); $R^3$ and $R^5$ represent hydrogen atom, or a halogen atom; $R^4$ represents hydroxyl group, a $C_{1-12}$ acyloxy group, a $C_{1-12}$ acyloxymethyloxy group, or an amino group], which is useful as a novel fluorescent labeling agent having a property of emitting intense fluorescence only after reacting with a thiol group.

(I)

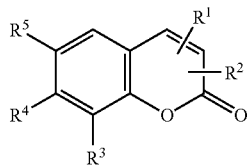

12 Claims, 1 Drawing Sheet

Cys was added to 10 μM solution of each dye,
and spectrum was measured at 0 or 100 μM Cys (100 mM NaPi buffer (pH=7.4)).

COUMARIN DERIVATIVE

TECHNICAL FIELD

The present invention relates to a novel coumarin derivative. More specifically, the present invention relates to a coumarin derivative having a feature of being substantially non-fluorescent, per se, and emitting intense fluorescence after reaction with a thiol group.

BACKGROUND ART

Direct fluorescent visualization of intracellular localization and dynamic behavior of proteins in cells and tissues in a living state is extremely important for elucidation of physiological functions of the proteins, so techniques utilizing fusion proteins comprising green fluorescent protein (GFP) have been widely used in recent years. However, a possibility of not being able to monitor target protein's behavior precisely is pointed out due to extremely large molecular size of GFP per se, a time lag between intracellular expression of GFP and formation of fluorophore, and the like.

As a method for introducing a fluorescent tag into a protein, it is known to use a thiol-reactive fluorescent labeling agent such as CPM, MDCC, fluorescein-5-maleimide and TMR-5-maleimide utilizing thiol groups in proteins (for example, thiol group of cysteine).

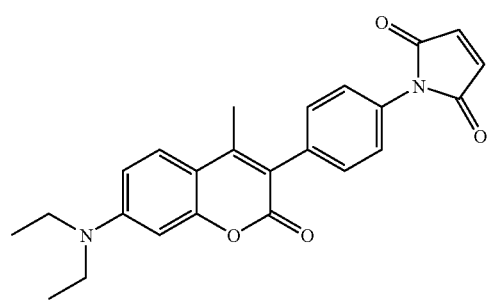

CPM

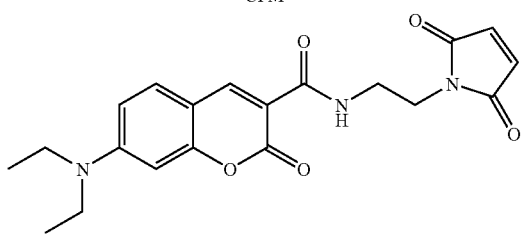

MDCC

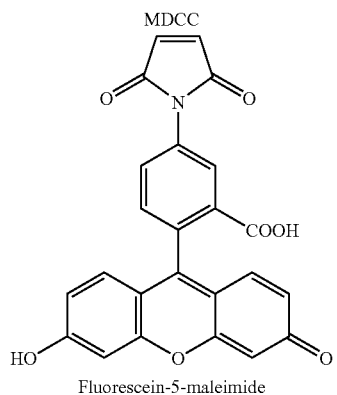

Fluorescein-5-maleimide

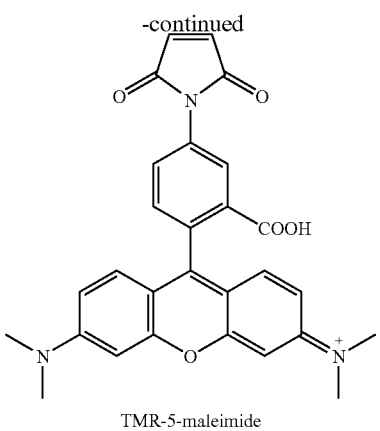

TMR-5-maleimide

Although the molecular size of these thiol-reactive fluorescent labeling agents is small, they have a problem that the difference of fluorescent intensities between before and after the reaction with a thiol group is small; specifically they may emit intense fluorescence before the reaction with thiol group, or they may have very weak fluorescence after being introduced into proteins by the reaction. Moreover, since the fluorescence tag is introduced by an addition reaction with arbitrary proteins containing cysteine residues with a thiol group, they have a problem that they cannot fluorescently label the target protein with fluorescence for fluorescent-based observation.

Under these circumstances, it has been desired to provide (1) a fluorescent labeling agent having small molecular size achieving significant difference of fluorescence intensities between before and after the reaction with thiol group, and (2) a means for introducing a fluorescent tag selectively only into target protein by fluorescent labeling agent whose molecular size is small to visualize the target protein fluorescently at high sensitivity.

DISCLOSURE OF THE INVENTION

An object of the present invention is to provide a novel fluorescent labeling agent having a property of emitting intense fluorescence only after reaction with a thiol group. Another object of the present invention is to provide a means for specifically introducing a fluorescent tag whose molecular size is small only into a target protein to visualize the protein fluorescently at high sensitivity.

The inventors of the present invention conducted various researches to achieve the aforementioned objects. As a result, they found that, in a coumarin derivative into which a substituent having maleimide group is introduced, the maleimide group acted as a PeT (Photoinduced Electron Transfer) acceptor to quench fluorescence of the coumarin as fluorophore, and after the nucleophilic addition of a nucleophilic agent such as a thiol group (for example, thiol group of cysteine) to maleimide group, the maleimide group no longer acted as a PeT acceptor, and thus the fluorescence of the coumarin was recovered. On the basis of this finding, they found that a thiol-reactive fluorescent labeling agent was successfully provided which was capable of switching fluorescence on and off by a reaction with a thiol group.

The inventors of the present invention also found that a coumarin derivative into which a substituent having two or more maleimide groups were introduced was substantially non-fluorescent. This is because all of the maleimide groups functioned as PeT acceptors, thus the coumarin's fluorescence as the fluorophore was quenched. On the other hand, only when all the maleimide groups underwent addition reactions with nucleophilic agents such as thiol groups the compound was highly fluorescent. On the basis of these findings, the inventors of the present invention found that when the aforementioned coumarin derivative into which a substituent having two or more maleimide groups were introduced reacted with a peptide having two or more neighboring cysteine residues, the compound provided fluorescent adduct only when all the maleimide groups underwent addition reactions with respective thiol groups of the cysteine residues, and that the compound was useful as a reagent for selectively labeling a peptide having two or more neighboring cysteine residues in the same molecule. The present invention was accomplished on the basis of the aforementioned findings.

The present invention thus provides a compound represented by the following general formula (I) or a salt thereof

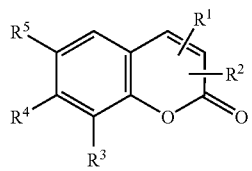
(I)

[wherein $R^1$ represents hydrogen atom, or a $C_{1-12}$ alkyl group; $R^2$ represents a $C_{1-12}$ alkyl group having one or more maleimide groups, an aryl group having two or more maleimide groups, a group represented by the following formula (A):

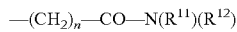
—$(CH_2)_n$—CO—N($R^{11}$)($R^{12}$)

(wherein $R^{11}$ and $R^{12}$ independently represent hydrogen atom, a $C_{1-12}$ alkyl group, a $C_{1-12}$ alkyl group having one or more maleimide groups, or an aryl group having one or more maleimide groups, provided that at least one of $R^{11}$ and $R^{12}$ represents a $C_{1-12}$ alkyl group having one or more maleimide groups, or an aryl group having one or more maleimide groups, and n represents an integer of 1 to 6), or a group represented by the following formula (B):

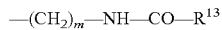
—$(CH_2)_m$—NH—CO—$R^{13}$ (wherein $R^{13}$ represents a $C_{1-12}$ alkyl group having one or more maleimide groups, or an aryl group having one or more maleimide groups, and m represents an integer of 1 to 6); $R^3$ and $R^5$ independently represent hydrogen atom, or a halogen atom; $R^4$ represents hydroxyl group, a $C_{1-12}$ acyloxy group, a $C_{1-12}$ acyloxymethyloxy group, or an amino group which may have one or two substituents].

The aforementioned compound or a salt thereof itself is substantially non-fluorescent, but when all the maleimide groups existing in the group represented by $R^2$ undergo addition reactions with thiol groups of a compound or biological substance containing the thiol group (for example, cysteine, peptide or protein containing a cysteine residue, etc.), the resulting adduct has highly fluorescent property.

According to a preferred embodiment of this invention, provided is the aforementioned compound of the formula (I) or a salt thereof, wherein $R^1$ is hydrogen atom; $R^2$ is a $C_{1-12}$ alkyl group having one maleimide group, a group represented by the aforementioned formula (A) (provided that one of $R^{11}$ and $R^{12}$ is hydrogen atom, or a $C_{1-12}$ alkyl group, and the other is a $C_{1-12}$ alkyl group having one maleimide group, or an aryl group having one maleimide group), or a group represented by the aforementioned formula (B) (provided that $R^{13}$ is a $C_{1-12}$ alkyl group having one maleimide group, or an aryl group having one maleimide group); each of $R^3$ and $R^5$ is independently hydrogen atom, or a halogen atom; and $R^4$ is hydroxyl group, a $C_{1-12}$ acyloxy group, a $C_{1-12}$ acyloxymethyloxy group, or an amino group which may have one or two substituents.

According to the most preferred embodiment of the aforementioned invention, provided is a compound represented by the following formula (III) or (IV), or a salt thereof:

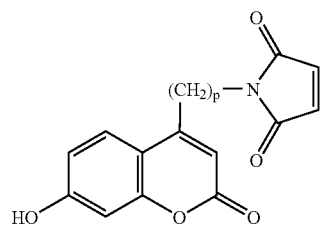
(III)

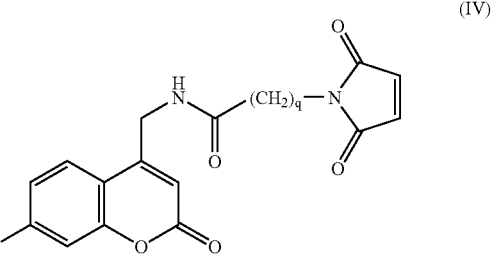
(IV)

(wherein p represents an integer of 1 to 6, and q represents an integer of 1 to 6).

According to another preferred embodiment of the invention, provided is the aforementioned compound of the formula (I) or a salt thereof, wherein $R^1$ is hydrogen atom; $R^2$ is a $C_{1-12}$ alkyl group having two or more maleimide groups, an aryl group having two or more maleimide groups, a group represented by the aforementioned formula (A) (provided that one of $R^{11}$ and $R^{12}$ is hydrogen atom or a $C_{1-12}$ alkyl group, and the other is a $C_{1-12}$ alkyl group having two or more maleimide groups, or an aryl group having two or more maleimide groups), a group represented by the aforementioned formula (A) (provided that each of $R^{11}$ and $R^{12}$ is independently a $C_{1-12}$ alkyl group having one or more maleimide groups, or an aryl group having one or more maleimide groups, and the total number of the maleimide groups existing in $R^{11}$ and $R^{12}$ is 2 or more), or a group represented by the aforementioned formula (B) (provided that $R^{13}$ is a $C_{1-12}$ alkyl group having two or more maleimide groups, or an aryl group having two or more maleimide groups); each of $R^3$ and $R^5$ is independently hydrogen atom or a halogen atom; and $R^4$ is hydroxyl group, a $C_{1-12}$ acyloxy group, a $C_{1-12}$ acyloxymethyloxy group, or an amino group which may have one or two substituents.

According to the most preferred embodiment of the aforementioned invention, provided is a compound represented by the following formula (V) or a salt thereof.

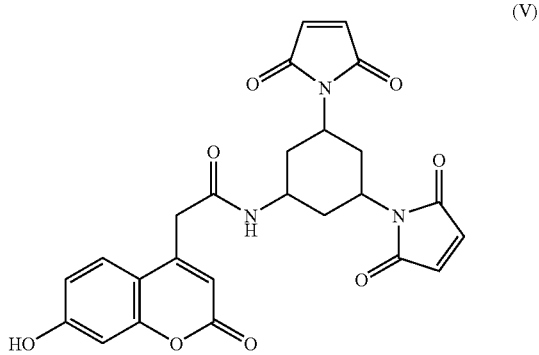

(V)

From another aspect, the present invention provides a compound represented by the aforementioned general formula (I) or a salt thereof, which is used for fluorescent labeling of a compound having a thiol group, or a peptide or protein containing a cysteine residue, and a fluorescent labeling agent used for fluorescent labeling of a compound having a thiol group, or a peptide or protein containing a cysteine residue, which comprises the compound represented by the aforementioned general formula (I) or a salt thereof. The compound represented by the aforementioned general formula (I) or a salt thereof undergoes addition reaction with a thiol group of a cysteine residue to provide a highly fluorescent adduct. As a result, a compound having the thiol group, or a peptide or protein containing the cysteine residue can be fluorescently labeled by the fluorescent adduct.

From a still further aspect, the present invention provides the aforementioned compound or a salt thereof having two or more maleimide groups, which is used for fluorescent labeling of a peptide or protein containing two or more neighboring cysteine residues in the same molecule. When not all the maleimide groups of the compound represented by the aforementioned general formula (I) or a salt thereof having two or more maleimide groups undergo addition reactions with thiol groups, the compound or a salt thereof is substantially non-fluorescent, on the other hand only when all the maleimide groups undergo addition reactions with thiol groups, the compound affords a highly fluorescent adduct. Therefore, when the compound represented by the aforementioned general formula (I) or a salt thereof having two or more maleimide groups reacts with a peptide or protein containing two or more neighboring cysteine residues in the same molecule, all of the maleimide groups very quickly undergo the addition reactions with thiol groups, and as a result, a highly fluorescent adduct is provided. By utilizing this property, a peptide or protein containing two or more neighboring cysteine residues in the same molecule can be selectively fluorescent labeled by using the aforementioned compound or a salt thereof.

The present invention further provides a method for fluorescently labeling a compound having a thiol group, or a peptide or protein containing a cysteine residue, which comprises the step of reacting a compound represented by the aforementioned general formula (I) or a salt thereof with a compound having a thiol group, or a peptide or protein containing a cysteine residue.

The compound represented by the aforementioned general formula (I) or a salt thereof has a property that the compound or a salt, per se, is substantially non-fluorescent, but provides a highly fluorescent adduct only when the compound reacts with a thiol group (for example, a thiol group of a low molecular weight compound such as cysteine, or a peptide or protein containing a cysteine residue). Therefore, the compound represented by the aforementioned general formula (I) or a salt thereof according to the present invention can be used as a fluorescent labeling agent for a substance having thiol group.

Further, the compound represented by the aforementioned general formula (I) or a salt thereof having two or more maleimide groups as $R^2$ has a property that the compound or a salt thereof, per se, is substantially non-fluorescent, and only when all of the maleimide groups react with thiol groups, the compound provides a highly fluorescent adduct. Therefore, by using this compound or a salt thereof, a peptide or protein containing neighboring cysteine residues in the same molecule, in a number not smaller than that of the maleimide groups, can be selectively fluorescent labeled.

BEST MODE FOR CARRYING OUT THE INVENTION

Figure 1:
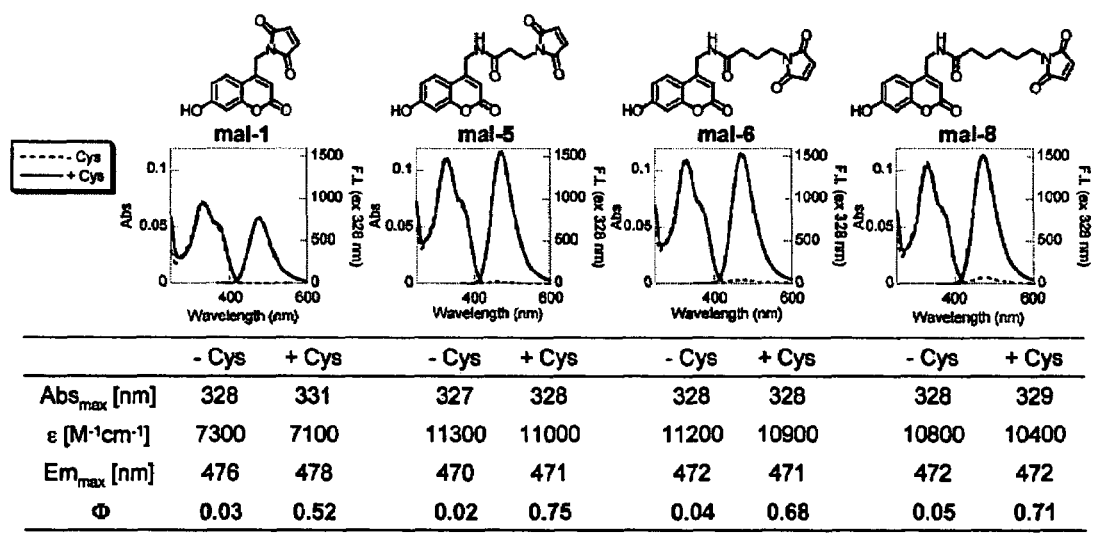
FIG. 1 shows optical characteristics of Compounds 1, 2, 3, and 4, and optical characteristics of cystein adducts of Compounds 1, 2, 3, and 4.

The meanings of the terms used in this specification are as follows.

The "alkyl group" or an alkyl moiety of a substituent containing the alkyl moiety (for example, alkoxyl group and the like) means a linear, branched, or cyclic saturated hydrocarbon group, or a combination thereof. More specifically, examples of the alkyl group include, methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, adamantyl group, and the like.

The "aryl group" means a monocyclic or condensed polycyclic aromatic hydrocarbon group or a monocyclic or condensed polycyclic aromatic heterocyclic group, and is preferably a monocyclic to tricyclic aromatic hydrocarbon group, or a monocyclic to tricyclic aromatic heterocyclic group, more preferably a monocyclic or bicyclic aromatic hydrocarbon group. Specific examples include phenyl group, naphthyl group, and the like.

An acyl moiety of a substituent containing the acyl moiety (for example, acyloxy group and the like) may be either an aliphatic acyl group or an aromatic acyl group, and hydrocarbon moiety of the aliphatic acyl group is a linear, branched, or cyclic hydrocarbon group, or a combination thereof, and may contain one or more unsaturated bonds. As an aromatic group of the aromatic acyl group, those explained for the aforementioned aryl group can be used.

The peptide includes dipeptides, tripeptides, oligopeptides (containing several to about 20 amino acid residues), polypeptides (containing more than 20 amino acid residues), and the like, and include those containing natural amino acid residues as well as non-naturally occurring amino acid residues.

In the compound represented by the aforementioned general formula (I), the $C_{1-12}$ alkyl group represented by $R^1$ is preferably methyl group or ethyl group, most preferably methyl group.

The $C_{1-12}$ alkyl group on which one or more maleimide groups are substituted, represented by $R^2$ in the compound represented by the aforementioned general formula (I), may be any linear, branched or cyclic $C_{1-12}$ alkyl group or a combination thereof on which one or more maleimide groups are substituted (although the maleimide groups may preferably substitute directly on the $C_{1-12}$ alkyl group, they may indirectly substitute on the $C_{1-12}$ alkyl group via an amide group, a phenylene group, or the like, and substitution positions of the maleimide groups on the $C_{1-12}$ alkyl group may be any substitutable positions, and are not particularly limited: the same shall apply to the term "substituted with maleimide groups" used in this specification). A $C_{1-6}$ linear alkyl group with one or more maleimide groups directly substituted is preferred. When $R^2$ is a $C_{1-12}$ linear alkyl group with one maleimide group directly substituted, the group is most preferably monomaleimidomethyl group.

Examples of the aryl group with two or more maleimide groups substituted represented by $R^2$ in the compound represented by the aforementioned general formula (I) include a phenyl group with two or three maleimide groups substituted, a monocyclic aromatic heterocyclic group with two or three maleimide groups (for example, triazenyl group) substituted, and the like, and a phenyl group with two or three maleimide groups substituted is preferred.

In the compound represented by the aforementioned general formula (I), $R^2$ is also preferably group represented by the formula (A). In the group represented by the formula (A), n represents an integer of 1 to 6, preferably an integer of 1 to 3, particularly preferably 1.

When $R^{11}$ or $R^{12}$ represents a $C_{1-12}$ alkyl group, this group is preferably ethyl group or methyl group, most preferably methyl group.

Examples of the $C_{1-12}$ alkyl group having one or more maleimide groups and represented by $R^{11}$ or $R^{12}$ include a linear, branched or cyclic $C_{1-12}$ alkyl group or a combination thereof with one or more maleimide groups substituted, and when $R^{11}$ or $R^{12}$ represents an $C_{1-12}$ alkyl group with one maleimide group substituted, the alkyl group is preferably a $C_{1-6}$ linear alkyl group, and more specifically, $R^{11}$ or $R^{12}$ is most preferably 2-maleimidoethyl group, 3-maleimidopropyl group, or 5-maleimidopentyl group. When $R^{11}$ or $R^{12}$ represents a $C_{1-12}$ alkyl group with two maleimide groups substituted, $R^{11}$ or $R^{12}$ is preferably a dimaleimide-substituted cyclohexyl group or a dimaleimide-substituted adamantyl group, most preferably 3,5-dimaleimidocyclohexyl group. When $R^{11}$ or $R^{12}$ represents a $C_{1-12}$ alkyl group with three maleimide groups substituted, the group is preferably a trimaleimide-substituted adamantyl group.

Examples of the aryl group having one or more maleimide groups represented by $R^{11}$ or $R^{12}$ include, for example, a phenyl group with one to three maleimide groups substituted, a monocyclic aromatic heterocyclic group with one to three maleimide groups (for example, triazinyl group) substituted, and the like, and a phenyl group with one to three maleimide groups substituted is preferred.

As for the combination of $R^{11}$ and $R^{12}$, when the total number of maleimide group existing in the groups represented by $R^{11}$ and $R^{12}$ is 1, it is preferred that one of $R^{11}$ and $R^{12}$ is hydrogen atom, and the other is a linear $C_{1-12}$ alkyl group with one maleimide group substituted. It is particularly preferred that one of $R^{11}$ and $R^{12}$ is hydrogen atom, and the other is 2-maleimidoethyl group, 3-maleimidopropyl group, or 5-maleimidopentyl group. When the total number of the maleimide groups existing in the groups represented by $R^{11}$ and $R^{12}$ is 2, it is preferred that $R^{11}$ and $R^{12}$ independently represent 2-maleimidoethyl group, 3-maleimidopropyl group, or 5-maleimidopentyl group, or one of $R^{11}$ and $R^{12}$ is hydrogen atom, and the other is a dimaleimide-substituted cyclohexyl group, and it is particularly preferred that one of $R^{11}$ and $R^{12}$ is hydrogen atom, and the other is 3,5-dimaleimidocyclohexyl group.

In the compound represented by the aforementioned general formula (I), it is also preferred that $R^2$ is a group represented by the formula (B). In the formula (B), m represents an integer of 1 to 6, preferably an integer of 1 to 3, most preferably 1. Examples of the $C_{1-12}$ alkyl group having one or more maleimide groups represented by $R^{13}$ include a linear, branched or cyclic $C_{1-12}$ alkyl group or a combination thereof with one or more maleimide groups substituted, and when $R^{13}$ represents a $C_{1-12}$ alkyl group with one maleimide group substituted, the alkyl group is preferably a $C_{1-6}$ linear alkyl group. More specifically, $R^{13}$ is most preferably 2-maleimidoethyl group, 3-maleimidopropyl group, or 5-maleimidopentyl group. When $R^{13}$ represents a $C_{1-12}$ alkyl group with two maleimide groups substituted, $R^{13}$ is preferably a dimaleimide-substituted cyclohexyl group or a dimaleimide-substituted adamantyl group, most preferably 3,5-dimaleimidocyclohexyl group. When $R^{13}$ represents a $C_{1-12}$ alkyl group with three maleimide groups substituted, the group is preferably a trimaleimide-substituted adamantyl group.

In the compound represented by the aforementioned general formula (I), $R^2$ preferably substitutes at the 3- or 4-position, most preferably at the 4-position, of the coumarin structure.

In the compound represented by the aforementioned general formula (I), although the halogen atom represented by $R^3$ or $R^5$ may be any of fluorine atom, chlorine atom, bromine atom, and iodine atom, the halogen is preferably fluorine atom or chlorine atom. When $R^3$ and $R^5$ represent fluorine atom or chlorine atom, pH stability of the fluorescent tag introduced into a peptide, oligopeptide, polypeptide or protein containing a cysteine residue by a reaction with the compound of the present invention may be improved.

As the $C_{1-12}$ acyloxy group represented by $R^4$ in the compound represented by the aforementioned general formula (I), a $C_{1-6}$ linear alkylcarbonyloxy group is preferred, and methylcarbonyloxy group is more preferred. As the $C_{1-12}$ acyloxymethyloxy group represented by $R^4$, a $C_{1-6}$ linear alkylcarbonyloxymethyloxy group is preferred, and methylcarbonyloxymethyloxy group is more preferred. The amino group represented by $R^4$ may have a substituent, more specifically, one or two substituents, and the group may be a primary to tertiary amino group. Examples of the substituent include a $C_{1-6}$ alkyl group, an acyl group, and the like, and more specifically, methyl group, ethyl group, and the like are preferred. Examples of the amino group having a substituent include, for example, methylamino group, dimethylamino group, diethylamino group, methylethylamino group, acetylamino group, and the like, and dimethylamino group, diethylamino group, and the like are preferred.

The compound of the present invention represented by the aforementioned general formula (I) can exist as an acid addition salt or base addition salt. Examples of the acid addition salt include, for example, mineral acid salts such as hydrochlorides, sulfates and nitrates, organic acid salts such as methanesulfonates, p-toluenesulfonates, oxalates, citrates and tartrates, and the like, and examples of the base addition salt include metal salts such as sodium salts, potassium salts, calcium salts and magnesium salts, ammonium salts, organic amine salts such as triethylamine salts, and the like. Besides these examples, the compound may form a salt with an amino acid such as glycine. The compound of the present invention or a salt thereof may exist also as a hydrate or a solvate, and any of these substances fall within the scope of the present invention.

The compound of the present invention represented by the aforementioned general formula (I) may have one or more asymmetric carbons depending on types of substituents, and stereoisomers including optical isomers based on one or more asymmetric carbons, diastereoisomers based on two or more asymmetric carbons, and the like as well as arbitrary mixtures of stereoisomers, racemates, and the like fall within the scope of the present invention.

The method for preparing typical examples of the compound of the present invention are specifically described in the examples of this specification. Therefore, those skilled in the art can prepare any compounds of the present invention represented by the aforementioned general formula (I) by properly choosing reaction starting materials, reaction conditions, reagents, and the like on the basis of these explanations, and by adding modifications and alterations to these methods if necessary.

The compound represented by the aforementioned general formula (I) or a salt thereof according to the present invention, per se, is substantially non-fluorescent, on the other hand when the compound of the present invention or a salt thereof reacts with a thiol group of a compound having the thiol group or of a protein or a peptide containing a cysteine residue to afford an adduct, the adduct is highly fluorescent. Therefore, the compound of the present invention can be used as a fluorescent labeling agent for a low molecular weight compound having a thiol group such as cysteine or a peptide or a protein containing a cysteine residue.

Moreover, when the compound of the present invention represented by the aforementioned general formula (I) or a salt thereof has two or more maleimide groups, the compound or a salt thereof has a property that it becomes a fluorescent adduct only when all of the maleimide groups undergo addition reactions with thiol groups. Therefore, if the compound of the present invention or a salt thereof having two or more maleimide groups in the same molecule is reacted with a substance having two or more neighboring cysteine residues in the same molecule, a fluorescent adduct is provided, whereas when the compound is reacted with a substance not having neighboring two or more cysteine residues, no fluorescent adduct is produced. More correctly, the compound of the present invention or a salt thereof provides a fluorescent adduct only when it reacts with a substance containing neighboring cysteine residues in a number not smaller than that of maleimide groups contained in the compound or a salt thereof. For example, when the compound or a salt thereof has three or more maleimide groups, it provides a fluorescent adduct only when it reacts with a substance containing three or more neighboring cysteine residues.

Therefore, by using the compound of the present invention or a salt thereof having two or more maleimide groups, a substance containing neighboring cysteine residues can be selectively labeled with fluorescence. For example, a system for specifically monitoring expression of a protein can be constructed, in which a peptide consisting about ten amino acid residues including two or three cysteine residues is prepared by using a molecular biological technique and then the peptide is introduced as a recognition tag into a protein as a target for observation, and the resulting protein is reacted with the compound of the present invention or a salt thereof having two or three maleimide groups, and thereby observation of intracellular localization, dynamic behaviors, and the like of the protein as the target for observation can be achieved.

From the entire disclosure of the specification, it can be understood by those skilled in the art that the term "neighboring" used in the present invention means not only a distance (interval) of two or more thiol groups in the primary structure, but also a spatial distance (interval) of two or more thiol groups, so long as turning on and off of fluorescence can be attained by the reaction of the compound of the present invention and thiol groups. More specifically, the term "neighboring" used in the present invention includes not only neighboring in the primary structure, but also neighboring in the secondary structure or tertiary structure. The methods for use specifically explained above are given only for exemplification, and ways of use of the compound of the present invention or a salt thereof are not limited to the aforementioned embodiments of uses.

EXAMPLES

The present invention will be explained more specifically with reference to examples. However, the scope of the present invention is not limited to the following examples.

Example 1

Synthesis of Compounds 1, 2, 3 and 4

The synthetic schemes for Compounds 1, 2, 3 and 4 are shown below. In the schemes, Ac represents acetyl group.

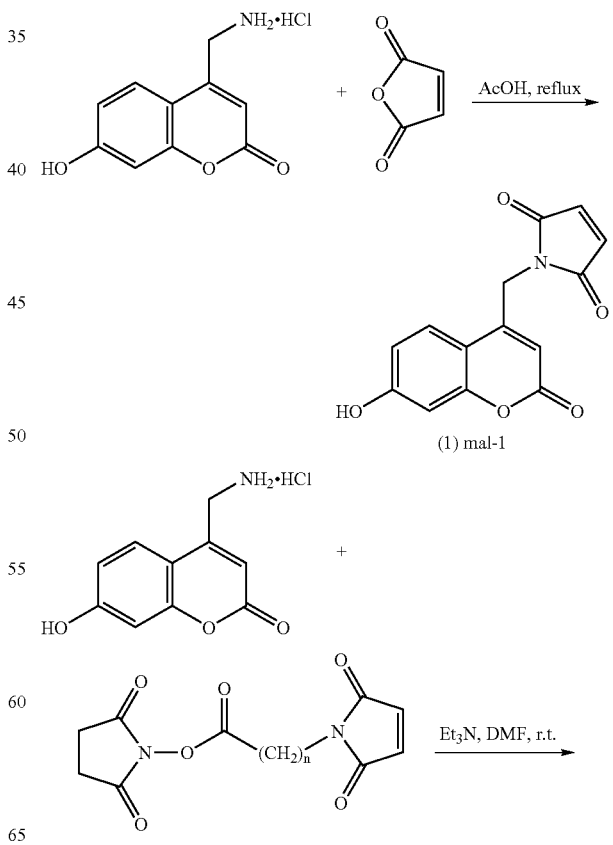

-continued

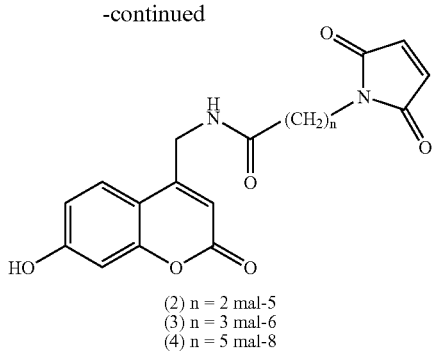

(2) n = 2 mal-5
(3) n = 3 mal-6
(4) n = 5 mal-8

(a) Synthesis of Compound 1 (mal-1)

4-Aminomethyl-7-hydroxycoumarin hydrochloride (32.4 mg, 0.14 mmol) was dissolved in acetic acid (10 mL), and maleic anhydride (17.6 mg, 0.18 mmol) was added to the solution, followed by stirring overnight under reflux by heating. Acetic acid was evaporated under reduced pressure, and the residue was purified by silica gel column chromatography (3% methanol/dichloromethane) to obtain Compound 1 (20.2 mg, 0.074 mmol, colorless powder, yield: 53%).

m.p. 262° C.

$^1$H NMR (300 MHz, DMSO-$d_6$) δ 4.78 (2H, s), 5.92 (1H, s), 6.74 (1H, d, J=2.4 Hz 6.82 (1H, dd, J=2.4, 8.8 Hz), 7.13 (2H, s), 7.71 (1H, d, J=8.8 Hz).

FT-IR (KBr, cm$^{-1}$) 3382, 3246, 3185, 3094, 2915, 1777, 1713, 1613, 1570, 1520, 1431, 1400, 1318, 1269, 1148, 997, 833, 696.

HR-MS (ESI$^-$) Calcd for [M–H]$^-$, 270.0403. Found, 270.0370.

(b) Synthesis of Compound 2 (mal-5)

4-Aminomethyl-7-hydroxycoumarin hydrochloride (30.6 mg, 0.13 mmol) was dissolved in acetonitrile (2 mL), and triethylamine (40 μL, 29.2 mg, 0.29 mmol) was added to the solution, followed by stirring on an ice bath. Then, N-succinimidyl 3-maleimidopropionate (37.5 mg, 0.14 mmol) was added to the mixture, and the mixture was stirred on the ice bath. After that N-(3-dimethylaminopropyl)-N'-ethylcarbodiimide (WSCD, 42.5 mg, 0.22 mmol) dissolved in dimethylformamide (5 mL) and a small amount of hydroxybenzotriazole (HOBt) were further added to the reaction mixture, and the mixture was further stirred. After the reaction was completed, the solvent was evaporated under reduced pressure, and saturated citric acid was poured to the residue. The mixture was extracted with ethyl acetate, and washed with saturated brine. The solvent was evaporated under reduced pressure, and the residue was purified by silica gel column chromatography (3% methanol/dichloromethane) to obtain Compound 2 (24.2 mg, 0.071 mmol, colorless powder, yield: 54%).

m.p. 207-210° C.

$^1$H NMR (300 MHz, DMSO-$d_6$) δ 3.28 (2H, m), 3.64 (2H, t, J=6.8 Hz), 4.39 (2H, d J=4.7 Hz), 5.98 (1H, s), 6.72 (1H, d, J=2.4 Hz), 6.78 (1H, dd, J=2.4, 8.3 Hz), 6.98 (2H, s), 7.61 (1H, d, J=8.3 Hz), 8.52 (1H, m),10.6 (1H, s). FT-IR (KBr, cm$^{-1}$) 3428, 3351, 3088, 2926, 2540, 1772, 1703, 1661, 1622, 1570, 1555, 1514, 1449, 1408, 1370, 1312, 1236, 1146, 995, 974, 835, 693.

MS (ESI$^-$) 341.07667, [M–H]$^-$.

HR-MS (ESI$^-$) Calcd for [M–H]$^-$, 341.0774. Found, 341.0749.

(c) Synthesis of Compound 3 (mal-6)

4-Aminomethyl-7-hydroxycoumarin hydrochloride (31.9 mg, 0.14 mmol) was dissolved in dimethylformamide (2 mL), and the solution was stirred on an ice bath. To the solution N-succinimidyl 4-maleimidobutyrate (43.1 mg, 0.15 mmol) was added, and the mixture was stirred at room temperature for 4 hours. After the reaction was completed, the solvent was evaporated under reduced pressure, and saturated citric acid was poured to the residue. The mixture was extracted with ethyl acetate, and washed with saturated brine. After the solvent was evaporated under reduced pressure, and the residue was purified by silica gel column chromatography (2% methanol/dichloromethane) to obtain Compound 3 (7.9 mg, 0.022 mmol, colorless powder, yield: 16%).

m.p. 200-201° C.

$^1$H NMR (300 MHz, DMSO-$d_6$) δ 1.75 (2H, m), 2.20 (2H, m), 3.41 (2H, m), 4.39 (2H, d, J=5.3 Hz), 6.01 (1H, s), 6.71 (1H, d, J=2.2 Hz), 6.77 (1H, dd, J=2.2, 8.7 Hz), 7.00 (2H, s), 7.62 (1H, d, J=8.8 Hz), 8.36 (1H, t, J=5.3 Hz).

FT-IR (KBr, cm$^{-1}$) 3295, 3080, 2928, 1709, 1655, 1613, 1570, 1549, 1449, 1410, 1313, 1267, 1147, 995, 847, 833, 696.

MS (ESI$^-$) 355.07, [M–H]$^-$.

HR-MS (ESI$^-$) Calcd for [M–H]$^-$, 355.0930. Found, 355.0888.

(d) Synthesis of Compound 4 (mal-8)

4-Aminomethyl-7-hydroxycoumarin hydrochloride (27.1 mg, 0.12 mmol) was dissolved in dimethylformamide (2 mL), and the solution was stirred on an ice bath. The mixture was added with N-succinimidyl 4-maleimidohexanoate (40.0 mg, 0.13 mmol), and stirred as it was at room temperature for 5 hours. After the reaction was completed, the solvent was evaporated under reduced pressure, and saturated citric acid was poured to the residue. The mixture was extracted with ethyl acetate, and subjected to a washing operation using saturated brine. After the solvent was evaporated under reduced pressure, and the residue was purified by silica gel column chromatography (3% methanol/dichloromethane) to obtain Compound 4 (14.0 mg, 0.037 mmol, colorless powder, yield: 30%).

m.p. 202-206° C.

$^1$H NMR (300 MHz, DMSO-$d_6$) δ 1.18-1.25 (2H, m), 1.43-1.57 (4H, m), 2.18 (2H, t, J=7.7Hz), 3.37-3.90 (2H, m), 4.41 (2H, d, J=5.0 Hz), 5.97 (1H, s), 6.71 (1H, d, J=2.0 Hz), 6.77 (1H, dd, J=2.2, 8.8 Hz), 6.99 (2H, s), 7.62 (1H, d, J=8.8 Hz), 8.35 (1H, t, J=5.0 Hz).

FT-IR (KBr, cm$^{-1}$) 3495, 3088, 2934, 2861, 1707, 1611, 1570, 1541, 1447, 1410, 1319, 1265, 1142, 995, 833, 696.

MS (ESI$^-$) 383.09, [M–H]$^-$.

HR-MS (ESI$^-$) Calcd for [M–H]$^-$, 383.1243. Found, 383.1254.

Example 2

Synthesis of Compound 8

The synthetic scheme for Compound 8 is shown below. In the scheme, Boc represents tert-butoxycarbonyl group.

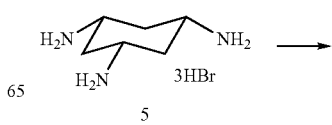

5

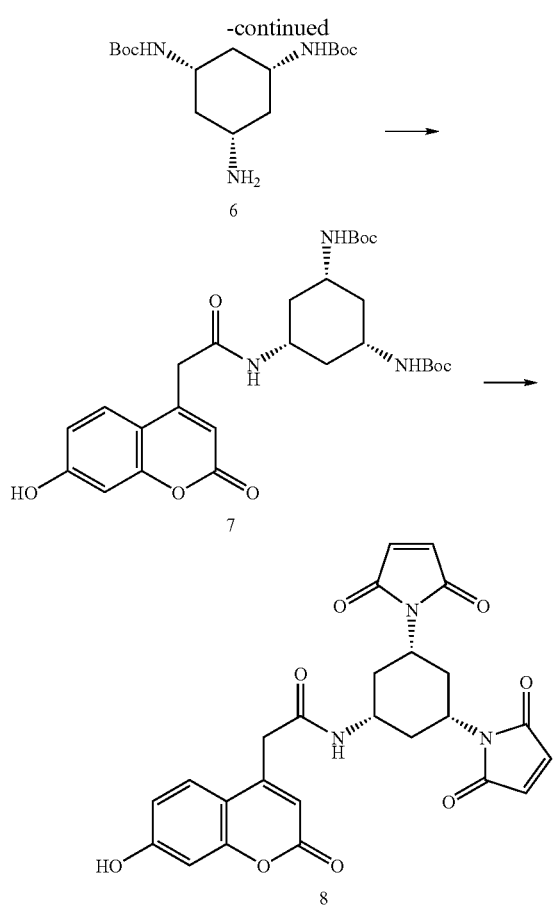

under reduced pressure, and the residue was purified by reverse phase HPLC (4% acetonitrile/water to 76% acetonitrile/water containing 0.1% trifluoroacetic acid (30 minutes)) to obtain Compound 7 (18.7 mg, 0.035 mmol, colorless powder, yield: 11.7%).

$^1$H-NMR (300 MHz, DMSO-$d_6$) δ 0.96-1.08 (3H, m), 1.78-1.81 (3H, m), 2.56 (2H, m), 3.58 (3H, m), 6.12 (1H, s), 6.70 (1H, d, J=2.2 Hz), 6.77 (1H, dd, J=2.2; 8.8 Hz), 6.87 (2H, d, J=7.9 Hz) 7.57 (1H, d, J=8.8 Hz), 8.19 (1H, d, J=7.5 Hz).

MS (ESI$^-$) 530.16, [M–H]$^-$.

(b) Synthesis of Compound 8

Compound 7 (8.6 mg, 0.016 mmol) was suspended in dichloromethane (3 mL) on an ice bath. The suspension was added with anisole (0.1 mL), and the mixture was added with trifluoroacetic acid (3 mL) by using a dropping funnel, and stirred for 45 minutes. Then, the solvent was evaporated under reduced pressure. The residue was dissolved in acetic acid (2 mL), and the mixture was added with maleic anhydride (8.6 mg, 0.088 mmol), and stirred overnight under reflux by heating. After the reaction was completed, the solvent was evaporated under reduced pressure, and the residue was purified by reverse phase HPLC (16% acetonitrile/water containing 0.1% TFA) to obtain Compound 8 (1.8 mg, 0.0037 mmol, colorless powder, yield: 23%).

$^1$H-NMR (300 MHz, Acetone-$d_6$) δ 1.29 (1H, s), 1.66-1.70 (1H, m), 2.10-2.16 (2H, m), 2.70-2.81 (2H, m), 3.71 (2H, s), 3.91-4.02 (1H, m), 4.12 (2H, tt, J=3.7; 8.8 Hz), 6.19 (1H, s), 6.73 (1H, d, J=2.4 Hz), 6.81 (4H, s), 6.82 (1H, dd, J=2.4; 8.7 Hz), 7.50 (1H, d, J=7.4 Hz), 7.67 (1H, d, J=8.7 Hz).

HR-MS (ESI$^-$) Calcd for [M–H]$^-$, 490.1250. Found, 490.1237.

Example 3

Reactions of Compounds 1, 2, 3 and 4 and Cysteine

Each of Compounds 1 to 4 was dissolved in a 100 mmol/L sodium phosphate buffer (pH=7.4) at a concentration of 10 μmol/L (containing 0.1% dimethyl sulfoxide), and the absorption spectrum and the fluorescence spectrum (excitation wavelength: 328 nm) were measured. Then, L-cysteine was added to the solution at a final concentration of 100 μmol/L, and the absorption spectrum and the fluorescence spectrum (excitation wavelength: 328 nm) were measured. Fluorescence quantum yield of each compound was calculated on the basis of that of quinine sulfate in a 0.1 mol/L sulfuric acid solution, which was taken as 0.577. The results are shown in FIG. 1. Fluorescence quantum yield of Compound 1 (mal-1), Compound 2 (mal-5), Compound 3 (mal-6), and Compound 4 (mal-8) provided by the present invention is fluorescence quantum yields lower than 0.05 or less, and hardly emitted fluorescence before addition reaction with a thiol group of cysteine. However, after addition reaction with a thiol group of cysteine, their fluorescence quantum yields become 0.52 to 0.75, and thus to give significantly fluorescent adducts.

Example 4

Reaction of Compound 8 and Cysteine

Compound 8 at a concentration of 5 μmol/L was added with N-acetylcysteine (NAC), Ac-AECACRA-OH peptide, or Ac-AECAACRA-OH peptide (C-terminus is carboxyl group, N-terminus is acetyl group (Ac), and amino acids are represented by the single letter codes), and fluorescence (a) Synthesis of Compound 7 cis-1,3,5-Cyclohexanetriamine trihydrobromide (Compound 5) was synthesized by referring to the methods described in Bioorg. Med. Chem. Lett., 6, 7, 807 (1996) and J. Biol. Inorg. Chem., 6, 4, 367 (2001).

cis-1,3,5-Cyclohexanetriamine trihydrobromide (Compound 5, 0.14 g, 0.38 mmol) was dissolved in methanol (5 mL). The solution was added with triethylamine (0.34 mL, 0.25 g, 2.5 mmol), then added with di-tert-butyl dicarbonate ((Boc)20, 0.17 g, 0.78 mmol) dissolved in methanol (5 mL) on an ice bath, and the mixture was stirred overnight. After the reaction was completed, the solvent was evaporated under reduced pressure, and dichloromethane was poured to the residue. The mixture was extracted with 1 N acetic acid, made alkaline with sodium hydroxide, and extracted with dichloromethane. The solvent was evaporated under reduced pressure to obtain Compound 6 (35.3 mg, colorless powder) as a crude product. This product was used for the next reaction without any treatment.

Figure 2:
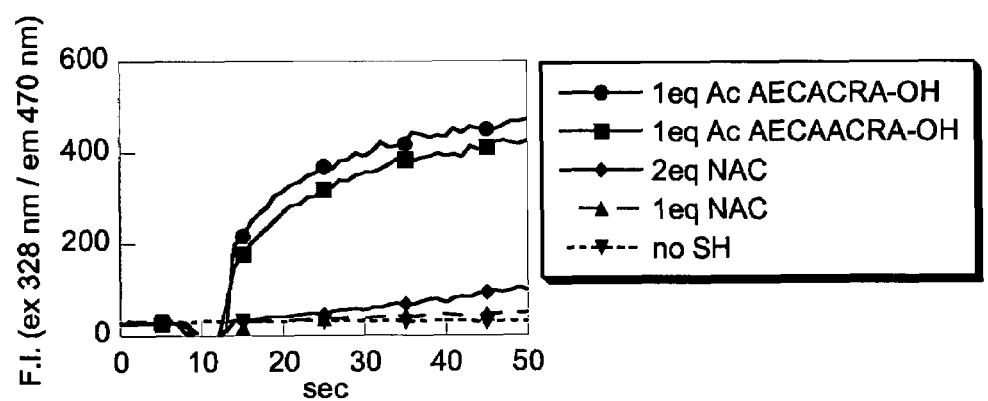
FIG. 2 shows results of measurement results of changes in fluorescence intensity over time observed when a substance having thiol group(s) (N-acetylcysteine, or a peptide containing two neighboring cysteine residues in the same molecule) was reacted with Compound 8.

7-Hydroxycoumarin-4-acetic acid (66.4 mg, 0.30 mmol) was dissolved in dimethylformamide (2 mL) on an ice bath. The solution was added with N-(3-dimethylaminopropyl)-N'-ethylcarbodiimide (WSCD, 0.18 g, 0.94 mmol) and 1-hydroxybenzotriazole (HOBt, 0.16 g, 1.2 mmol), and the resulting mixture was stirred for 30 minutes. Then Compound 6 (crude product, 0.10 g) was added to the solution, and stirred overnight at room temperature. After the reaction was completed, the reaction mixture, into which saturated citric acid solution was poured, was extracted with ethyl acetate, and washed with saturated brine. The solvent was evaporated intensity was measured. For the reaction mixture, a 100 mmol/L sodium phosphate buffer (pH=7.4, containing 0.5% dimethyl sulfoxide as a cosolvent) was used. The results are shown in FIG. 2.

Compound 8 was substantially non-fluorescent even after the reaction with one molecule of cysteine. However, it efficiently reacted with the peptides containing two neighboring cysteine residues in the same molecule to give intensely fluorescent adducts. Therefore, it was demonstrated that the compound of the present invention having two or more maleimide groups was capable of reacting with the peptides containing neighboring cysteine residues and selectively labeling the substances with fluorescence. Moreover, it was confirmed that by introducing a side chain containing such a peptide into an target protein, the target protein was specifically labeled with fluorescence.

What is claimed is:

1. A compound represented by the following formula (IV), or a salt thereof:

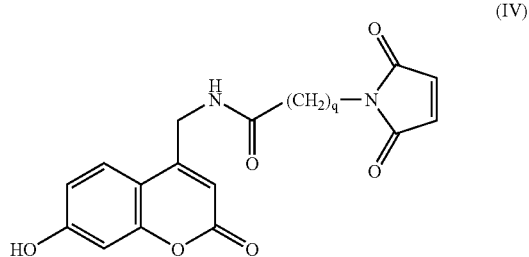

wherein q represents an integer of 1 to 6.

2. The compound or a salt thereof according to claim 1, which is used for fluorescent labeling of a compound having a thiol group, or a peptide or protein containing a cysteine residue.

3. A fluorescent labeling agent used for fluorescent labeling of a compound having a thiol group, or a peptide or protein containing a cysteine residue, which contains the compound or a salt thereof according to claim 1.

4. A compound according to claim 1, wherein q represents 2.

5. The compound or a salt thereof according to claim 4, which is used for fluorescent labeling of a compound having a thiol group, or a peptide or protein containing a cysteine residue.

6. A fluorescent labeling agent used for fluorescent labeling of a compound having a thiol group, or a peptide or protein containing a cysteine residue, which contains the compound or a salt thereof according to claim 4.

7. A compound according to claim 1, wherein q represents 3.

8. The compound or a salt thereof according to claim 7, which is used for fluorescent labeling of a compound having a thiol group, or a peptide or protein containing a cysteine residue.

9. A fluorescent labeling agent used for fluorescent labeling of a compound having a thiol group, or a peptide or protein containing a cysteine residue, which contains the compound or a salt thereof according to claim 7.

10. A compound according to claim 1, wherein q represents 5.

11. The compound or a salt thereof according to claim 10, which is used for fluorescent labeling of a compound having a thiol group, or a peptide or protein containing a cysteine residue.

12. A fluorescent labeling agent used for fluorescent labeling of a compound having a thiol group, or a peptide or protein containing a cysteine residue, which contains the compound or a salt thereof according to claim 10.

* * * * *